US006615084B1

(12) United States Patent
Cigaina

(10) Patent No.: US 6,615,084 B1
(45) Date of Patent: Sep. 2, 2003

(54) PROCESS FOR ELECTROSTIMULATION TREATMENT OF MORBID OBESITY

(75) Inventor: Valerio Cigaina, Treviso (IT)

(73) Assignee: Transneuronix, Inc., Mt. Arlington, NJ (US)

( * ) Notice: Subject to any disclaimer, the term of this patent is extended or adjusted under 35 U.S.C. 154(b) by 230 days.

(21) Appl. No.: 09/713,556

(22) Filed: Nov. 15, 2000

(51) Int. Cl.[7] .................................................. A61N 1/08

(52) U.S. Cl. ......................... 607/40; 607/116; 607/133; 600/424

(58) Field of Search ........................... 607/40, 115, 116, 607/133; 600/424, 407, 408; 128/899

(56) References Cited

U.S. PATENT DOCUMENTS

| | | | |
|---|---|---|---|
| 2,865,376 A | | 12/1958 | Pellier et al. |
| 3,760,812 A | | 9/1973 | Timm et al. |
| 4,444,207 A | | 4/1984 | Robicsek |
| 4,475,560 A | | 10/1984 | Tarjan et al. |
| 4,524,771 A | | 6/1985 | McGregor et al. |
| 4,901,722 A | | 2/1990 | Noguchi |
| 5,059,207 A | | 10/1991 | Shah |
| 5,100,431 A | | 3/1992 | Buster et al. |
| 5,188,104 A | * | 2/1993 | Wernicke et al. ............. 607/40 |
| 5,217,471 A | | 6/1993 | Burkhart |
| 5,242,458 A | | 9/1993 | Bendel et al. |
| 5,292,344 A | | 3/1994 | Douglas |
| 5,423,872 A | | 6/1995 | Cigaina |
| 5,423,876 A | | 6/1995 | Camps et al. |
| 5,433,728 A | | 7/1995 | Kim |
| 5,450,739 A | | 9/1995 | Bogart et al. |
| 5,489,294 A | | 2/1996 | McVenes et al. |
| 5,690,691 A | | 11/1997 | Chen et al. |
| 5,716,392 A | | 2/1998 | Bourgeois et al. |
| 5,772,693 A | * | 6/1998 | Brownlee ................... 607/123 |
| 5,836,994 A | | 11/1998 | Bourgeois |
| 5,861,014 A | | 1/1999 | Familoni |
| 5,995,872 A | | 11/1999 | Bourgeois |
| 6,146,391 A | | 11/2000 | Cigaina |

FOREIGN PATENT DOCUMENTS

| | | |
|---|---|---|
| DE | 44 02 058 | 1/1994 |
| WO | WO 97/41921 | 11/1997 |

OTHER PUBLICATIONS

Cigaina, V., "Implantable Gastric Stimulation for the Treatment of Morbid Obesity", Transneuronix Inc., Rev. 2, Nov. 1, 1999.

Cigaina, V., "Implantable Gastric Stimulation for the Treatment of Morbid Obesity", Transneuronix Inc., Rev. 1, Oct. 3, 1999.

* cited by examiner

*Primary Examiner*—Tu Ba Hoang
(74) *Attorney, Agent, or Firm*—Fitch, Even, Tabin & Flannery

(57) ABSTRACT

An improved process using electrostimulation for treating obesity, especially morbid obesity, and other syndromes related to motor disorders of the stomach is provided. The improved method of this invention provides electrostimulation on the lesser curvature of the stomach, preferably on the lower or distal end of the lesser curvature, which provides improved control of obesity and other syndromes related to motor disorders of the stomach. In one embodiment, the process employs stimulation of the lesser curvature at a rate of about 2 to about 14 pulses/minute with each pulse lasting about 0.5 to about 4 seconds such that there is a pause of about 3 to about 30 between the pulses. Preferably, the pulse rate is about 12 pulses/minute with each pulse lasting about 2 seconds with a pause of about 3 seconds between pulses. Preferably, the pulse amplitude is about 0.5 to about 15 milliamps. More preferable, each pulse consists of a train of micro-bursts with a frequency of about 5 to about 100 $sec^{-1}$.

24 Claims, 2 Drawing Sheets

PROCESS FOR ELECTROSTIMULATION TREATMENT OF MORBID OBESITY

FIELD OF THE INVENTION

The present invention relates to an improved process using electrostimulation for treating obesity, especially morbid obesity, and other syndromes related to motor disorders of the stomach. The improved method of this invention provides electrostimulation on the lesser curvature of the stomach which provides improved control of obesity and other syndromes related to motor disorders of the stomach.

BACKGROUND OF THE INVENTION

The modern surgical orientation with regard to obesity generally entails the reduction of gastric compliance, with the aim of limiting the subject's ability to ingest food, or of reducing the food absorption surface by shortening or bypassing part of the digestive canal; both aims are sought in some surgical procedures. Until recently, surgery was the only therapy that ensures real results in patients who have exceeded obesity values close to or greater than about 40 BMI (ratio of weight to the square of the height).

All of the major surgical procedures (e.g., removal or blocking off of a portion of the stomach) currently in use have some immediate and/or delayed risks. Thus, surgery is usually considered as an extreme solution when all less invasive procedures fail. Furthermore, even surgical treatment fails in some cases, thereby requiring the surgeon to restore the original anatomical situation.

More recently, methods have been successfully employed whereby an electrostimulation device is implanted on the stomach wall. For example, U.S. Pat. No. 5,423,872 (Jun. 13,1995) provided a process for the treatment of obesity and related disorder employing an electrostimulator or pacemaker attached to the antrum or greater curvature of the stomach. U.S. Pat. No. 5,690,691 (Nov. 25, 1997) provided a portable or implantable gastric pacemaker including multiple electrodes positionable on the inner or outer surface of an organ in the gastrointestinal tract which are individually programmed to deliver a phased electrical stimulation to pace peristaltic movement of material through the gastrointestinal tract. Although these methods have generally been successful, it is still desirable to provide improved methods for such treatments. The present invention provides such an improved process.

SUMMARY OF THE INVENTION

The present invention provides a process for treating obesity and/or related motor disorders by providing an electrostimulation or pacemaker device attached to the lesser curvature of the stomach. Preferably, the electrostimulation or pacemaker device provides electrostimulation to the lower or distal end of the lesser curvature (i.e., towards the pylorus). Preferably, the process of this invention employs stimulation of the lesser curvature at a rate of about 2 to about 14 pulses/minute with each pulse lasting about 0.5 to about 4 seconds such that there is a pause of about 3 to about 30 between the pulses. More preferably, the pulse rate is about 12 pulses/minute with each pulse lasting about 2 seconds with a pause of about 3 seconds between pulses. Preferably, the pulse amplitude is about 0.5 to about 15 milliamps. More preferable, each pulse consists of a train of micro-bursts with a frequency of about 5 to about 100 $sec^{-1}$.

The process of the present invention involves treatment of obesity and other syndromes related to motor disorders of the stomach of a patient. The process comprises artificially altering, using sequential electrical pulses for preset periods of time, the natural gastric motility of the patient to prevent or slow down stomach emptying, thereby slowing food transit through the digestive system.

The present invention provides a method for treatment of a motor disorder of a patient's stomach, said method comprising implanting an electrostimulation device comprising one or more electrostimulation leads and an electrical connector for attachment to a pulse generator such that the one or more electrostimulation leads are attached to, or adjacent to, lesser curvature of the patient's stomach, whereby electrical stimulation can be provided to the lesser curvature through the one or more electrostimulation leads; and supplying electrical stimulation to the lesser curvature through the one or more electrostimulation leads.

This invention also provides a method for treatment of a motor disorder of a patient's stomach, said method comprising implanting an electrostimulation device comprising an elongated body with a proximal and a distal end and having one or more electrostimulation leads and an electrical connector for attachment to a pulse generator at the proximal end such that the one or more electrostimulation leads are attached to, or adjacent to, lesser curvature of the patient's stomach, whereby electrical stimulation can be provided to the lesser curvature through the one or more electrostimulation leads and whereby, once the electrostimulation device is implanted, the one or more electrostimulation leads are at the distal end of the elongated body; and supplying electrical stimulation to the lesser curvature through the one or more electrostimulation leads.

DETAILED DESCRIPTION OF THE PREFERRED EMBODIMENTS

The present invention provides a process for treating obesity and/or related motor disorders by providing an electrostimulation or pacemaker device attached to the lesser curvature of the stomach. Preferably, the electrostimulation or pacemaker device provides electrostimulation to the distal end of the lesser curvature (i.e., towards the pylorus). Preferably, the process of this invention employs stimulation of the lesser curvature at a rate of about 2 to about 14 pulses/minute with each pulse lasting about 0.5 to about 4 seconds such that there is a pause of about 3 to about 30 between the pulses. More preferably, the pulse rate is about 12 pulses/minute with each pulse lasting about 2 seconds with a pause of about 3 seconds between pulses. Preferably, the pulse amplitude is about 0.5 to about 15 milliamps. More preferable, each pulse consists of a train of micro-bursts with a frequency of about 5 to about 100 $sec^{-1}$.

The process of the present invention involves treatment of obesity and other syndromes related to motor disorders of the stomach of a patient. The process comprises artificially altering, using sequential electrical pulses for preset periods of time, the natural, gastric motility of the patient to prevent or slow down stomach emptying, thereby slowing food transit through the digestive system. It has been surprisingly found that placement of an electrostimulator on the lesser curvature, and even more preferably on the distal end of the lesser curvature near or adjacent to the angular notch, provides superior results as compared to placement on the fundus, greater curvature, or antrum. Although not wishing to be limited by theory, it is thought that this improvement is at least in part due to the greater concentration of nerve fibers in the region of the lesser curvature as well as less expansion and contraction of the stomach muscles in the region of the lesser curvature during digestion processes. The placement of the electrostimulation device in the area of the lesser curvature is a somewhat easier surgical laparoscopic procedure due to the easier access.

Figure 1:
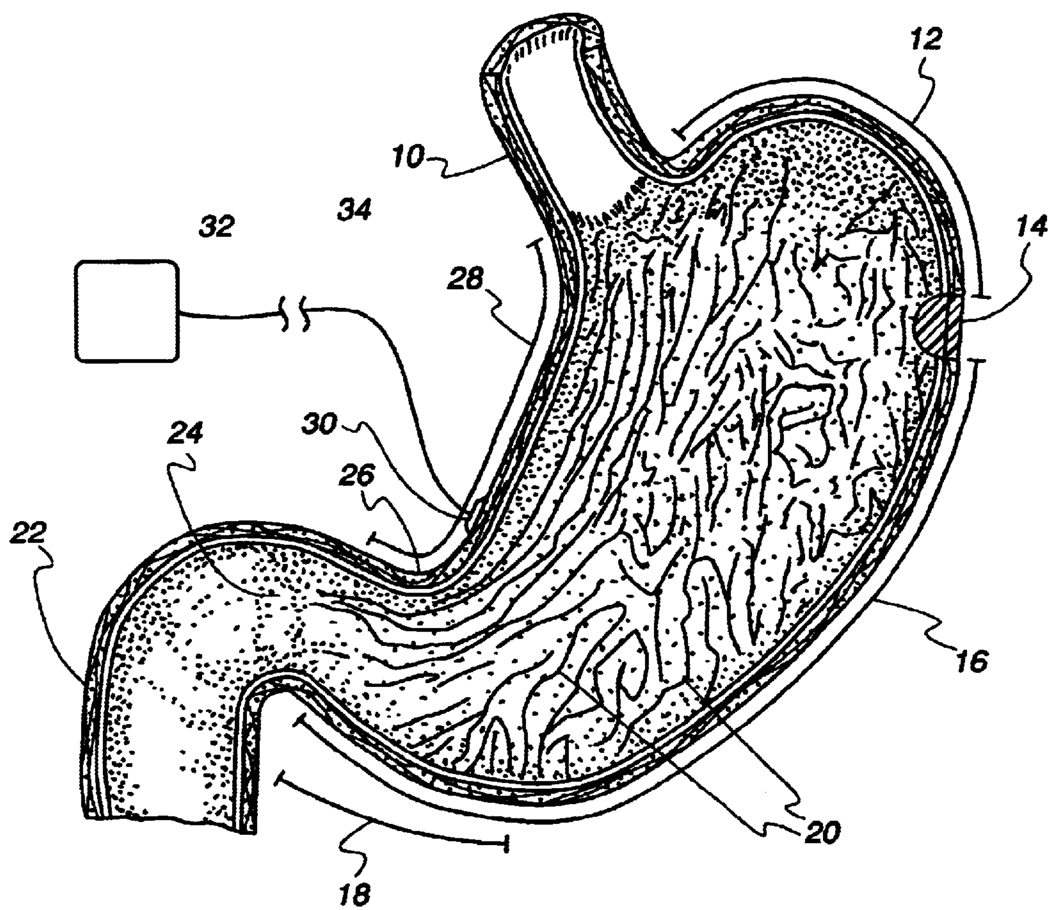
FIG. 1 is a sectional view of a stomach showing the device of the invention in place along the lesser curvature of the stomach.

In order to further clarify the process and device for treating obesity and syndromes related to motor disorders of the stomach of a patient, according to the invention, the motor physiology of the gastric viscus is briefly described. As shown in FIG. 1, the stomach is supplied by the esophagus 10, and has the fundus ventriculi 12, the cardia 11, the body or corpus ventriculi 13, the antrum 18, the pylorus 24, the duodenum 22, and mucous folds or rugae 20. The stomach is generally divided into two parts as regards its motility: the fundus ventriculi 12, which has tonic wall movements, and the central part or corpus 13, which is characterized by phasic activity. Propulsive gastric movements begin at a point proximate to the greater curvature 16 which is not clearly identified anatomically and is termed "gastric pacemaker" 14. The gastric pacemaker 14 sends electrical pulses (depolarization potential) at a rate of approximately three times per minute which spread in an anterograde direction along the entire stomach in the form of waves which have a general sinusoidal shape.

The antrum 18 of the stomach has a continuous phasic activity which has the purpose of mixing the food which is present in the stomach. The passage of food into the duodenum 22 is the result of a motility coordinated among the antrum 18, pylorus 24, and duodenum 22. The gastric pacemaker 14 spontaneously and naturally generates sinusoidal waves along the entire stomach; these waves allow the antrum 18, in coordination with the pylorus 24 and duodenum 22, to allow food to pass into the subsequent portions of the alimentary canal (i.e., intestines).

Now that the known physiology of the gastric motility of a mammal, such as a human being, has been established, the process according to the invention consists in artificially altering, by means of sequential electrical pulses and for preset periods of time, the natural gastric motility of a patient and/or the time and manner of contraction of the lower esophageal and pyloric sphincters to prevent emptying or slow down gastric transit, to prevent duodenal acidification during interdigestive phases, and/or to prevent gastric reflux in the last portion of the esophagus. More particularly, the sequential electrical pulses are generated by an electrical stimulator 30 which is applied by laparoscopic means to a portion of the seromuscular layer of the lesser curvature 28 of the stomach of the patient. In this manner, the electrical stimulus generates one or more sinusoidal waves 16 which start in the lesser curvature 28 and add, more or less synchronously, with those which correspond to the natural electrical activity of the stomach when emptying procedures are activated in the stomach. Preferably, the electrical stimulator 30 is placed on the distal end (i.e., at or near the angular notch 26) of the lesser curvature 28. The electrical stimulator induces in the stomach a motor incoordination (so-called antral tachygastria) in order to slow down or even prevent gastric transit through the pylorus into the intestine located downstream and thus allow treatment of obesity related to hyperalimentation, to modulate fasting gastric hypermotility for the treatment of relapsing duodenal ulcer in anxious subjects, and/or to improve the functionality of the lower esophageal and/or pyloric sphincters in treating reflux esophagitis and gastropathy induced by duodenogastric reflux.

The electrical stimulator or electrocatheter, according to the motor phenomenon to be corrected (e.g., induction of antral tachygastria in obesity, modulation of gastric hypermotility in anxious subjects, increase in sphincter function in reflux disorders), has a purpose-specific and potentially patientspecific frequency, intensity, duration, and period of stimulation, in addition to having a specific gastric location (i.e., lesser curvature 28) for application of the electrostimulation according to the type of disorder. The stimulator can be programmed both for continuous stimulation and for "on demand" stimulation (i.e., at the onset of a particular electrical activity which can be detected by the stimulator itself through the electrocatheter (if modified to monitor electrical activity) or under the control of the patient or medical personnel).

Figure 2:
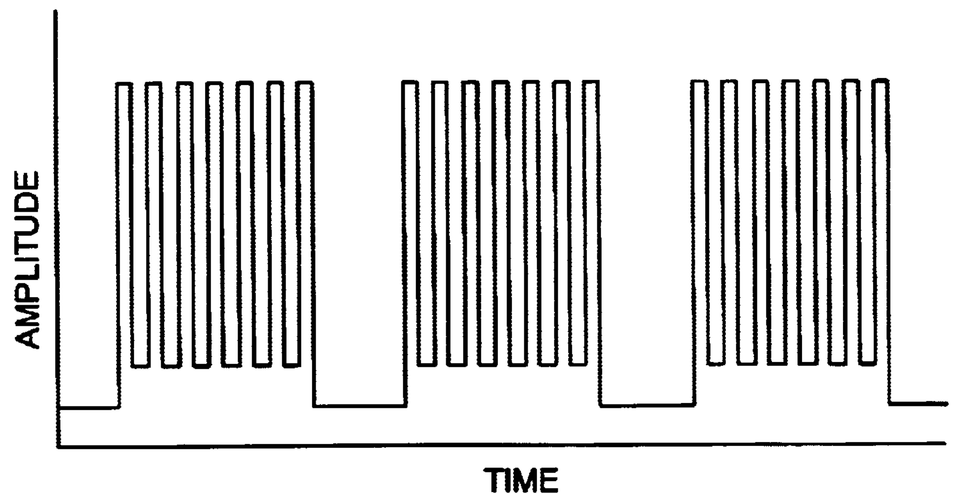
FIG. 2 is a schematic representation (not to scale) of a preferred microburst pulse train provided to the lesser curvature of the stomach.

The electrical stimulator 30, in order to allow to perform iatrogenic tachygastria, preferably has a preset operating frequency and period which may obviously vary according to the alteration of stomach motility to be obtained and/or to the pathological condition of the patient. Generally, the electrical stimulator 30 has an operating frequency of about 2 to about 15 pulses per minute. Preferably, the process of this invention employs stimulation of the lesser curvature at a rate of about 2 to about 14 pulses/minute with each pulse lasting about 0.5 to about 4 seconds such that there is a pause of about 3 to about 30 between the pulses. The electrical discharge of each pulse can vary from approximately 1 to 15 volts for voltage-controlled stimulation and from 2 to 15 milliamperes for constant current stimulation. More preferably, the pulse rate is about 12 pulses/minute with each pulse lasting about 2 seconds with a pause of about 3 seconds between pulses. Preferably, the pulse amplitude is about 0.5 to about 15 milliamps. More preferable, each pulse consists of a train of micro-bursts with a frequency of about 5 to about 100 $sec^{-1}$. FIG. 2 generally illustrates a preferred microburst pulse train provided to the lesser curvature of the stomach.

The present invention generally uses conventional laparoscopic or minimally invasive surgical techniques to place the desired electrostimulation device 30 on, or adjacent to, the lesser curvature 28, and preferably on the distal portion of the lesser curvature (i.e., adjacent to the angular notch 26). As shown in FIG. 1, the electrostimulation device 30 is attached to a suitable pulse generator 32 via leads 34. Conventional electrostimulation devices may be used in the practice of this invention. Such devices include, for example, those described in U.S. Pat. No. 5,423,872 (Jun. 3, 1995) (an implantable gastric electrical stimulator at the antrum area of the stomach which generates sequential electrical pulses to stimulate the entire stomach, thereby artificially altering the natural gastric motility to prevent emptying or to slow down food transit through the stomach); U.S. Pat. No. 5,690,691 (Nov. 25, 1997) (a portable or implantable gastric pacemaker employing a number of electrodes along the greater curvature of the stomach for delivering phased electrical stimulation at different locations to accelerate or attenuate peristaltic movement in the GI tract); U.S. Pat. No. 5,836,994 (Nov. 17, 1998) (an implantable gastric stimulator which incorporates direct sensing of the intrinsic gastric electrical activity by one or more sensors of predetermined frequency bandwidth for application or cessation of stimulation based on the amount of sensed activity); U.S. Pat. No. 5,861,014 (Jan. 19, 1999) (an implantable gastric stimulator for sensing abnormal electrical activity of the gastrointestinal tract so as to provide electrical stimulation for a preset time period or for the duration of the abnormal electrical activity to treat gastric rhythm abnormalities); U.S. patent application Ser. No. 09/424,324 (filed Jan. 26, 2000) (now U.S. Pat. No. 6,321,124 (Nov. 20, 2001)) (implant device equipped with tines to help secure it in the appropriate location); U.S. Pat. No. 6,041,258 (Mar. 21, 2000) (electrostimulation device with improved handle for laparoscopic surgery); U.S. patent application Ser. No. 09/640,201 (filed Aug. 16, 2000) (electrostimulation device attachable to enteric or endoabdominal tissue or viscera which is resistance to detachment); U.S. Pat. No. 6,542,776 (issued Apr. 1, 2003; filed Dec. 17, 1999) based on U.S. Provisional Application Serial Nos. 60/129,198, 60/129,199, and 60/129,209 (all filed Apr. 14, 1999); U.S. Provisional Application Serial No. 60/466,387 (filed Dec. 17, 1999); and U.S. Provisional Patent Application Serial No. 60/235,660 (filed Sep. 26, 2000) entitled "Method and Apparatus for Intentional Impairment of Gastric Motility and/or Efficiency by Triggered Electrical Stimulation of the Gastric Tract with Respect to the Intrinsic Gastric Electrical Activity." All of these patents, patent applications, provisional patent applications, and/or publications are hereby incorporated by reference.

Preferred electrostimulation devices include electrocatheters having an elongated body with a distal end having an electrostimulation lead or leads mounted on, or attached to, the stomach in the region of the lesser curvature and a proximal end for attachment to a pulse generator. The electrostimulation lead or leads are attached to a power source through, or with, the pulse generator. Such preferred electrostimulation devices are described in, for example, U.S. patent application Ser. No. 09/424,324 (filed Jan. 26, 2000) (now U.S. Pat. No. 6,321,124 (Nov. 20, 2001)), and U.S. patent application Ser. No. 09/640,201 (filed Aug. 16, 2000).

Figure 3:
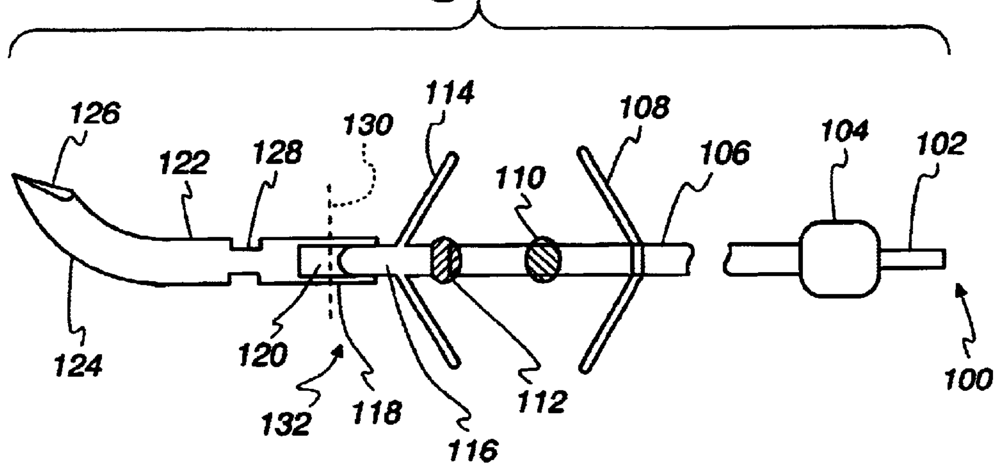
FIG. 3 illustrates an elongated electrostimulation device suitable for use in the present invention.

FIG. 3 provides an example of one electrostimulation device which can be used in the present invention. As described in more detail in U.S. Pat. No. 6,321,124, a stylet 122 is attached to the elongated body 106 at distal end 132. The stylet 122 in this embodiment is attached to the elongated body 106 using a flexible tube 118 (preferable medical-grade silicone similar to the insulating cover of the elongated body 106) that fits over the end 116 of elongated body 106 and the hub 120 of stylet 122. The connection may be strengthen, if desired, using medical-grade adhesive and/or a thin wire joining the stylet 122 and the elongated body 106. Of course, if such a wire is used to strengthen the connection, it should be non-conducting or electrically isolated from the electrical circuit used for stimulation. The stylet 122 has a curved portion 124 and a cutting edge 126 to allow the stylet 122 to easily penetrate the tissue to which the electrostimulation device is to be attached. Once the electrostimulation device has been properly located within the tissue to be stimulated (i.e., such that poles 110 and 112 contact the desired tissue), the stylet 122 may be removed by cutting along line 130. Preferably the stylet 122 has one or more flattened portions 128 to help the surgeon grasp, manipulate, and guide the implant device to the proper position using forceps or other surgical instruments. The elongated body 106 has two opposite set of tines or wings 114 and 108 with the appropriate poles 110 and 112 located there between. The tines or wings 114 and 108 lock the elctrostimulation device in place once it has been properly positioned. The elongated body 106 terminates in an electrical terminal having electrical poles 102 and 104 at proximal end 100. Once in place, the two poles 104 and 102 of the electrical terminal are attached to a power source (not shown). One pole 104 of the electrical terminal is electrically connected to one pole 112 and the other pole 110 of the electrical terminal is electrically connected to the other pole 110 through the elongated body. The electrical circuit is completed via the tissue to be stimulated and/or monitored. Thus, as those skilled in the art will understand, the overall electrical circuit within the implant device runs from one pole 104 of the electrical terminal along a first electrical path through the elongated body 106 to electrical pole 112, through the tissue to be stimulated to the other electric pole 110, and then from the other electric pole 110 through a second and separate electric path through the elongated body 106 to the other pole 102 in the electrical terminal. As those skilled in the art will also realize, the materials of construction and the methods of making the electrical circuit for the implant devices of this invention, including the poles as well as the internal electrical connections, are well known in the art. Further details concerning the placement and use of such an elongated electrocatheter can be found in U.S. Pat. No. 6,321,124. Details regarding other suitable electrocatheters can be found in the other patents and applications incoporated by reference above.

Although the present invention is especially adapted for treatment of obesity and/or control of weight, it may also be employed in treatment regimes involving other stomach-related disorders including, for example, relapsing peptic duodenal ulcer of anxious subjects, gastric peptic disorders induced by duodenogastric reflux, esophageal peptic disorders induced by gastroesophageal reflux, and the like.

The present methods can also be used in combination with electrostimulation of other parts of the gastrointestinal tract. For example, electrostimulation could be applied to the region of the lesser curvature as well as one or more location within the gastrointestinal tract. The sites of electrostimulation could be phased or non-phased in relation to one another.

The methods and electrostimulators used in the present invention are susceptible to numerous modifications and variations, all of which are within the scope of the present inventive concept. Furthermore, all the details may be replaced with technically equivalent elements. The materials employed, the shapes, and the dimensions of the specific electrostimulators may be varied according to the requirements.

I claim:

1. A method for treatment of a motor disorder of a patient's stomach, said method comprising implanting an electrostimulation device comprising at least one electrostimulation lead and an electrical connector for attachment to a pulse generator such that the at least one electrostimulation lead is attached to, or adjacent to, lesser curvature of the patient's stomach, whereby electrical stimulation can be provided to the lesser curvature through the at least one electrostimulation lead; and supplying electrical stimulation to the lesser curvature through the at least one electrostimulation lead.

2. The method of claim 1, wherein the at least one electrostimulation lead is attached to, or adjacent to, the lesser curvature at the lesser curvature's lower end.

3. The method of claim 1, wherein the electrical stimulation supplied to the lesser curvature has an operating frequency of about 2 to about 15 pulses per minute.

4. The method of claim 2, wherein the electrical stimulation supplied to the lesser curvature at a rate of about 2 to about 15 pulses per minute.

5. The method of claim 3, wherein the rate of the electrical stimulation supplied to the lesser curvature is about 2 to about 14 pulses/minute with each pulse lasting about 0.5 to about 4 seconds such that there is a pause of about 3 to about 30 between the pulses.

6. The method of claim 4, wherein the rate of the electrical stimulation supplied to the lesser curvature is about 2 to about 14 pulses/minute with each pulse lasting about 0.5 to about 4 seconds such that there is a pause of about 3 to about 30 between the pulses.

7. The method of claim 3, wherein each pulse consists of a train of micro-bursts with a frequency of about 5 to about 100 $sec^{-1}$.

8. The method of claim 4, wherein each pulse consists of a train of micro-bursts with a frequency of about 5 to about 100 $sec^{-1}$.

9. The method of claim 5, wherein each pulse consists of a train of micro-bursts with a frequency of about 5 to about 100$sec^{-1}$.

10. The method of claim 6, wherein each pulse consists of a train of micro-bursts with a frequency of about 5 to about 100 $sec^{-1}$.

11. The method of claim 9, wherein the motor disorder is obesity.

12. The method of claim 10, wherein the motor disorder is obesity.

13. A method for treatment of a motor disorder of a patient's stomach, said method comprising implanting an electrostimulation device comprising an elongated body with a proximal and a distal end and having at least one electrostimulation lead and an electrical connector for attachment to a pulse generator at the proximal end such that the at least one electrostimulation lead is attached to, or adjacent to, lesser curvature of the patient's stomach, whereby electrical stimulation can be provided to the lesser curvature through the at least one electrostimulation lead and whereby, once the electrostimulation device is implanted, the at least one electrostimulation lead is at the distal end of the elongated body; and supplying electrical stimulation to the lesser curvature through the at least one electrostimulation lead.

14. The method of claim 13, wherein the at least one electrostimulation lead is attached to, or adjacent to, the lesser curvature at the lesser curvature's lower end.

15. The method of claim 13, wherein the electrical stimulation supplied to the lesser curvature has an operating frequency of about 2 to about 15 pulses per minute.

16. The method of claim 14, wherein the electrical stimulation supplied to the lesser curvature at a rate of about 2 to about 15 pulses per minute.

17. The method of claim 15, wherein the rate of the electrical stimulation supplied to the lesser curvature is about 2 to about 14 pulses/minute with each pulse lasting about 0.5 to about 4 seconds such that there is a pause of about 3 to about 30 between the pulses.

18. The method of claim 16, wherein the rate of the electrical stimulation supplied to the lesser curvature is about 2 to about 14 pulses/minute with each pulse lasting about 0.5 to about 4 seconds such that there is a pause of about 3 to about 30 between the pulses.

19. The method of claim 15, wherein each pulse consists of a train of micro-bursts with a frequency of about 5 to about 100 $sec^{-1}$.

20. The method of claim 16, wherein each pulse consists of a train of micro-bursts with a frequency of about 5 to about 100 $sec^{-1}$.

21. The method of claim 17, wherein each pulse consists of a train of micro-bursts with a frequency of about 5 to about 100 $sec^{-1}$.

22. The method of claim 18, wherein each pulse consists of a train of micro-bursts with a frequency of about 5 to about 100 $sec^{-1}$.

23. The method of claim 21, wherein the motor disorder is obesity.

24. The method of claim 22, wherein the motor disorder is obesity.

* * * * *